United States Patent [19]
Burris

[11] Patent Number: 5,207,993
[45] Date of Patent: * May 4, 1993

[54] BATCH LIQUID PURIFIER

[76] Inventor: William A. Burris, 7 E. Jefferson Cir., Pittsford, N.Y. 14534

[*] Notice: The portion of the term of this patent subsequent to Jan. 21, 2009 has been disclaimed.

[21] Appl. No.: 670,690

[22] Filed: Mar. 18, 1991

Related U.S. Application Data

[63] Continuation-in-part of Ser. No. 575,622, Aug. 31, 1990, Pat. No. 5,082,558.

[51] Int. Cl.$^5$ .............................................. B01D 11/04
[52] U.S. Cl. ...................................... 422/256; 210/138; 210/143; 210/188; 422/116; 422/186.07; 422/186.1; 422/305
[58] Field of Search ................ 422/28, 116, 119, 255, 422/256, 305, 292, 186.07, 186.08, 186.1, 907; 210/188, 167, 136, 138, 143, 194

[56] References Cited

U.S. PATENT DOCUMENTS

| | | | |
|---|---|---|---|
| Re. 32,672 | 5/1988 | Huth et al. ............................ | 252/45 |
| 746,292 | 12/1903 | Clark .................................... | 210/285 |
| 2,328,640 | 7/1943 | Gage .................................... | 422/186.15 |
| 2,350,842 | 6/1944 | Tsuno ................................... | 361/270 |
| 3,382,980 | 5/1968 | Silva .................................... | 210/123 |
| 3,445,001 | 5/1969 | LaRuas ................................. | 210/98 |
| 3,692,180 | 9/1972 | LaRaus ................................. | 210/139 |
| 3,699,776 | 10/1972 | LaRaus ................................. | 62/157 |
| 3,726,404 | 4/1973 | Troglione ............................. | 210/139 |
| 3,742,301 | 6/1973 | Burris ................................... | 317/4 |
| 3,823,728 | 7/1974 | Burris ................................... | 137/88 |
| 3,841,997 | 10/1974 | McGee ................................. | 210/260 |
| 3,910,296 | 10/1975 | Karageozian et al. ................. | 134/2 |
| 4,019,986 | 4/1977 | Burris et al. .......................... | 210/139 |
| 4,029,817 | 6/1977 | Blanco et al. ........................ | 424/80 |
| 4,098,964 | 7/1978 | Reber ................................... | 429/86 |
| 4,179,616 | 12/1979 | Coviello et al. ...................... | 422/186.07 |
| 4,230,571 | 10/1980 | Dadd .................................... | 422/29 |
| 4,395,346 | 7/1983 | Kleist .................................... | 252/106 |
| 4,445,893 | 5/1984 | Bodicky ................................ | 605/165 |
| 4,517,159 | 5/1985 | Karlson ................................. | 422/20 |
| 4,555,335 | 11/1985 | Burris ................................... | 210/192 |
| 4,599,166 | 7/1986 | Gesslauer ............................ | 210/96.1 |
| 4,619,763 | 10/1986 | O'Brien ................................. | 210/177 |
| 4,670,178 | 6/1987 | Huth et al. ............................ | 252/106 |
| 4,703,761 | 11/1987 | Rathbone et al. . | |
| 4,746,489 | 5/1988 | Arnold .................................. | 128/675 |
| 4,776,343 | 10/1988 | Hubbard et al. ..................... | 210/192 |
| 4,842,723 | 6/1989 | Parks et al. .......................... | 210/95 |
| 5,082,558 | 1/1992 | Burris ................................... | 210/167 |

Primary Examiner—Robert J. Warden
Assistant Examiner—Krisanna M. Thornton
Attorney, Agent, or Firm—Eugene Stephens & Associates

[57] ABSTRACT

A batch liquid purifier using a reservoir, an ozone generator, and a pumping system is arranged for contacting the liquid with an ozone containing gas so that it is purified either during a direct outflow to a purified liquid chamber or during a circulational flow back to the reservoir. The flow circuit can include a liquid gas separator and venting of gas to atmosphere via an ozone concentration reducer. Pumping, valving, and controls can be accomplished in a variety of ways.

55 Claims, 6 Drawing Sheets

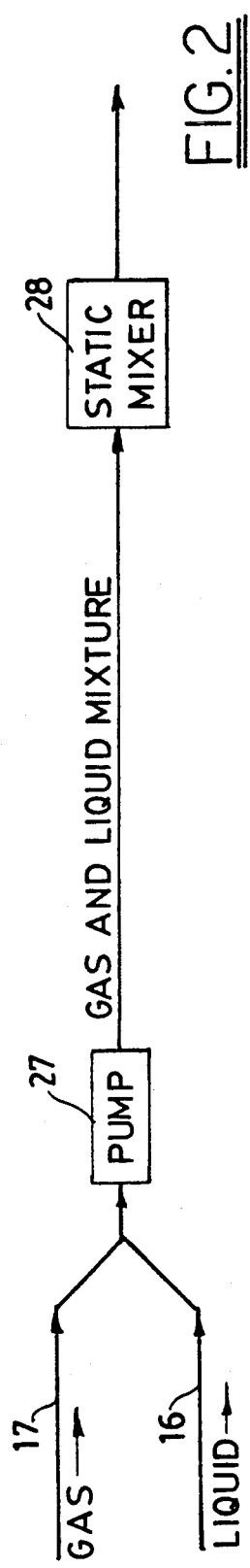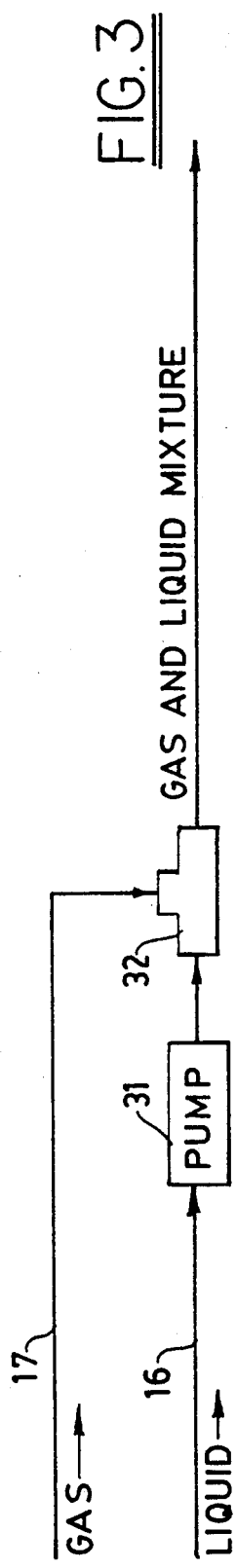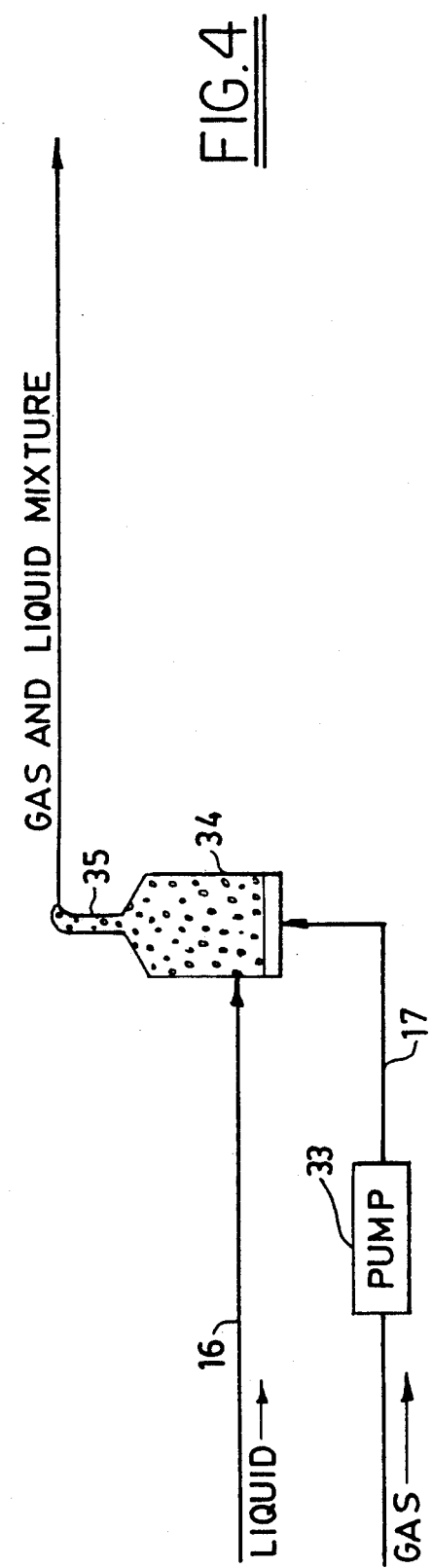

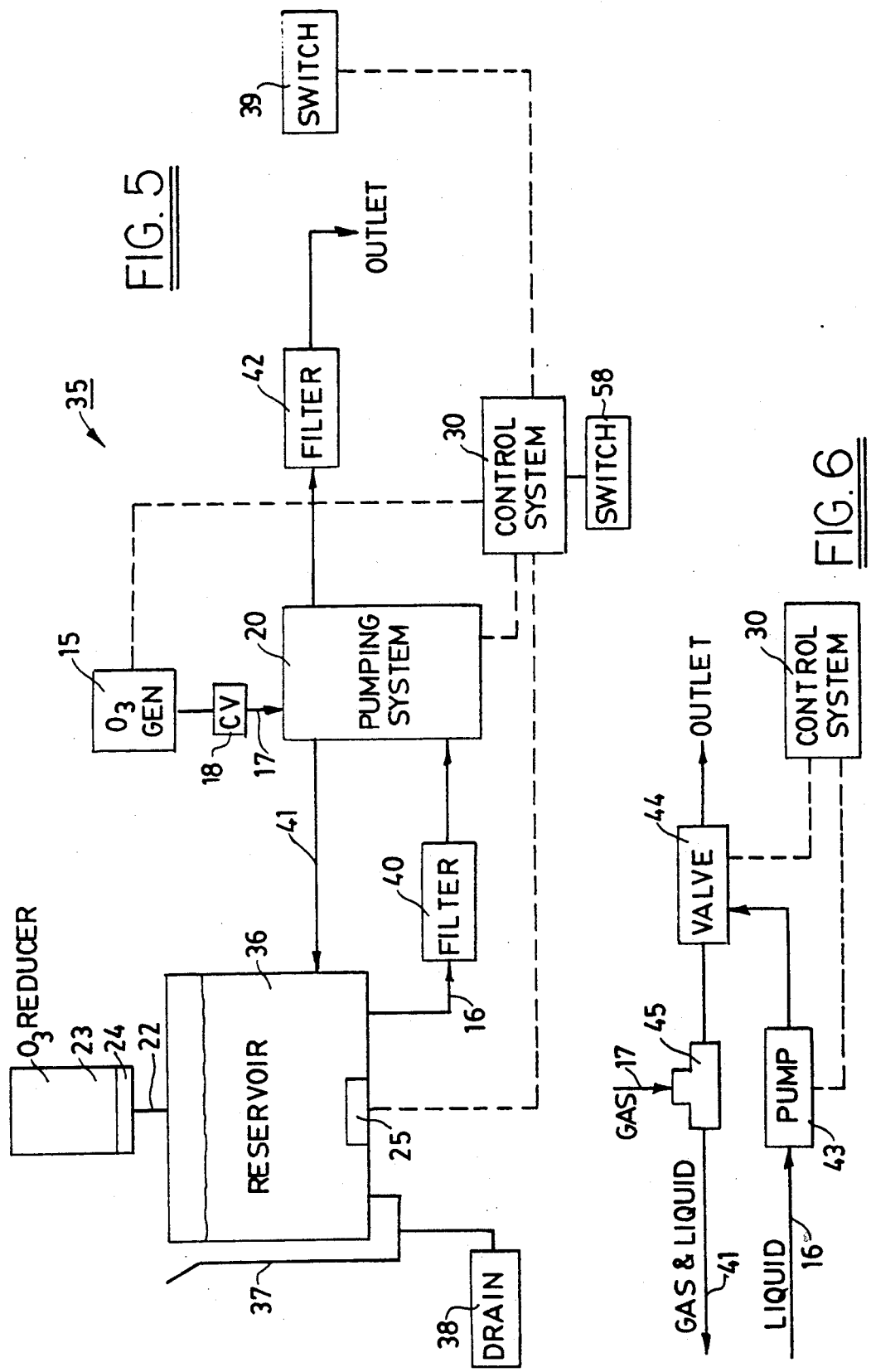

BATCH LIQUID PURIFIER

This application is a Continuation-In-Part of my co-pending parent application Ser. No. 575,622, filed 31 August 1990, entitled CONTACT LENS PURIFICATION SYSTEM, now U.S. Pat. No. 5,082,558, issued Jan. 21, 1992.

TECHNICAL FIELD

This invention involves ozone purification of batches of liquid with equipment made small enough to operate on a countertop or in space available below a counter.

BACKGROUND

By this invention, I have reduced the size, complexity, and expense of equipment for purifying or treating batches of liquid with ozone; and by carefully selecting and combining components, I have been able to make smaller scale ozone purification equipment operate conveniently and reliably for safely purifying liquid batches within reasonably short times. Equipment according to my invention can be operated on a residential countertop or in a small space under a counter, for example, to produce purified liquid batches less than 20 liters in size.

The purifier of this invention includes a generator that makes an ozone containing gas and operates on a batch basis with a reservoir or chamber sized for holding less than 20 liters of liquid. By one arrangement, the liquid flows through a passageway from the reservoir to a purified or treated liquid container, and a gas passageway from the generator leads ozone to the liquid passageway. A pumping system causes the liquid to flow through the liquid passageway and causes the gas to contact the liquid with ozone to effect its purification as it proceeds toward the purified liquid container. The pumping rate and the dimensions of the liquid and gas passageways determine the flow rates of the liquid and the ozone containing gas. In a recirculating arrangement, the liquid flows through a liquid passageway leading back to the reservoir, and a pumping system is arranged for flowing the liquid into contact with the ozone containing gas in a circulational path during purification. A pumping system can also be arranged for contacting the liquid with ozone containing gas during a purification cycle, and then outputting purified liquid during an output cycle.

BRIEF DESCRIPTION OF THE DRAWINGS

All of the drawings are partially schematic diagrams of different preferred embodiments of my batch liquid purifier. Each embodiment includes an ozone generator, a reservoir of liquid to be purified, a pumping system for bringing ozone into contact with the liquid to be purified, a reducer for diminishing the concentration of any escaping ozone and a controller to ensure that liquid purifying treated occurs. The various embodiments of the drawings differ from each other in that:

FIGS. 2-4 schematically show three preferred alternatives for pumping systems usable in the embodiments of FIGS. 1 and 5-9.

FIG. 5 schematically shows a bypass system that can purify liquid while it is pumped through a circulational path from and back to a reservoir, with an alternate route leading to an outlet.

FIG. 6 shows a pump, valve, and control system usable for the pumping system of FIG. 5.

DETAILED DESCRIPTION

Figure 1:
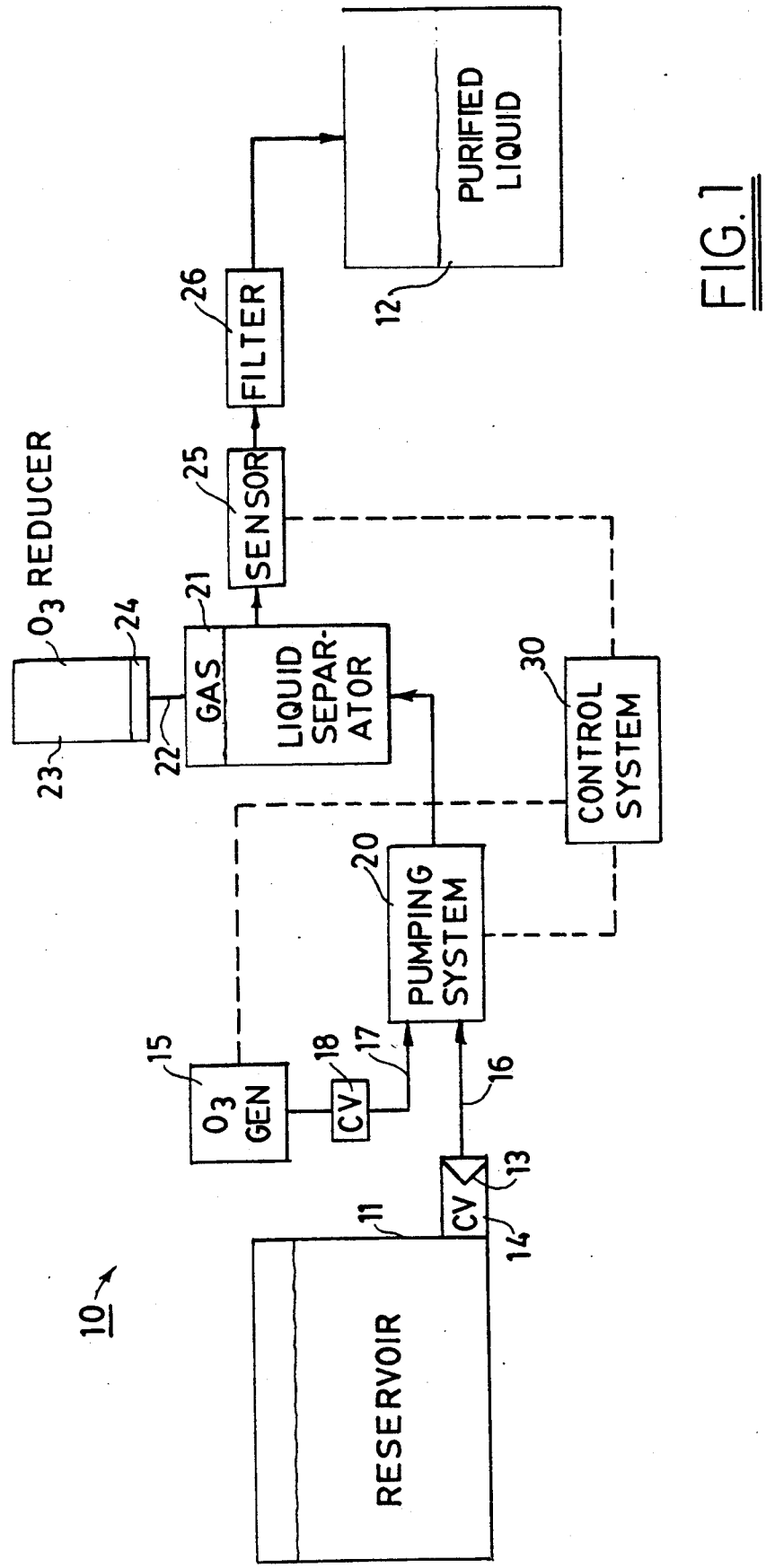
FIG. 1 shows an in-line system for pumping liquid from a reservoir to a purified liquid container while contacting the liquid with ozone to ensure its purification.

The preferred embodiments of the drawings have comparative advantages in features such as convenience, reliability, safety, cost, and compactness. Different embodiments, using different combinations of such features, may be preferred for different users with different desires. The embodiments will be explained in the order presented in the drawings, but this does not imply any similar order of importance. Also, some of the different features that are illustrated in the drawings can be interchanged among the various embodiments, and the drawings are arranged to illustrate the different features that can be combined, and not to delimit one combination of features from another.

The reasons that the purifier embodiments can be varied so extensively include the many different uses for liquid purifiers and the correspondingly different considerations for expense, space requirements, and batch size. One important use is purifying water for drinking and cooking purposes. This can be done on or below a countertop with batches sized for coffeepots and hand-held pitchers. Different users will require different levels of sophistication in convenience and extent of automatic performance. Water can also be purified on a batch basis for small scale requirements in laboratories, offices, and industries and for purposes such as disinfection. The liquid to be purified is not necessarily water, and my purifiers can be applied to purifying saline solution, for example. This could be desirable in an optometrist's office, for rinsing and storing contact lenses.

The liquid purifier 10 of FIG. 1 purifies raw liquid as it flows from reservoir 11 to purified liquid container 12. A pumping system 20 directs the liquid flow from reservoir 11 to container 12 and contacts the liquid with an ozone containing gas from generator 15 so that the liquid is purified as the flow occurs.

Reservoir 11 and container 12 are sized to hold less than 20 liters of liquid and can be made small enough to hold one coffee pot full of liquid, for example. Reservoir 11 can have a quickly releasable connection 13 that includes a check valve 14 for connecting and disconnecting reservoir 11 with liquid flow line 16 leading to pumping system 20. A gas flow line 17 leads from ozone generator 15, preferably via a check valve 18, to convey a gas and ozone mixture to pumping system 20. Besides conventional check valving, check valve 18 can be formed of a porous hydrophobic material that allows gas to pass through but prevents any liquid backflow from reaching generator 15. This is especially desirable when generator 15 is the preferred corona discharge generator that would be damaged by presence of any liquid. Suitable porous hydrophobic materials can include hydrophobic resin or plastic materials that are made porous to allow passage of gas, but block the passage of liquid. Porous inorganic materials may also be usable for this. The entire material does not need to be hydrophobic, so long as a hydrophobic material is arranged to serve as a liquid barrier combined with an otherwise porous material. These considerations also apply to other uses of porous hydrophobic materials in my purifiers, as explained below.

Although ambient air is a simple and preferred input for generator 15, it is also possible to use dried air that has passed through a dryer to help keep moisture out of generator 15. Another possibility is supplying oxygen from a small container serving as the input to generator 15, which can produce more ozone from an oxygen supply than from an air supply.

Pumping system 20 can take several forms, as explained more fully below. Generally, it draws liquid from reservoir 11 via liquid line 16 and contacts the liquid with ozone contained in a gas drawn via line 17 so that the ozone purifies or treats the liquid before it reaches chamber 12. In the embodiment of FIG. 1, the gas and liquid output from pumping system 20 is directed to a gas and liquid separator 21. The gas drawn from generator 15 and combined with the liquid by pumping system 20 separates from the liquid in separator 21 and is vented to atmosphere. This preferably occurs through an ozone reducer 23 that reduces the concentration of ozone in any gas entering the atmosphere. Reducer 23 contains at least one of several materials that are available for reducing the ozone concentration or changing the ozone into ordinary oxygen so that raw ozone does not escape into the atmosphere. Even if raw ozone were to escape through vent 22, however, it should not present any health hazard in the small quantities used for operating system 10.

There are several ways that gas and liquid separator 21 can operate. The liquid level is preferably controlled by a float valve, which has the advantage of keeping the liquid pressurized. Gravity can also be used to provide a liquid surface above which gas can rise. Another possibility is to arrange a porous hydrophobic element to form a barrier for liquid, while allowing gas to pass. The liquid and gas separation can occur separate from a liquid reservoir or purified liquid storage, or can be combined with these, as explained below.

When reducer 23 is used and is filled with a catalytic or reactive material that reduces the ozone concentration or changes the ozone into oxygen, it is important that liquid not reach the material within reducer 23, because liquid would impair its action. Working against this is the fact that gas bubbles enter separator 21 and burst at the liquid surface there, creating spray droplets that can enter vent 22. Baffles are one possibility for keeping these spray droplets out of reducer 23, but baffles would not block liquid flow if the system were overturned. What I prefer, therefore, is a porous hydrophobic element 24 that allows gas, but not liquid, to enter reducer 23.

From gas and liquid separator 21, liquid proceeds to purified liquid container 12. In doing so, purified liquid can flow past sensor 25, to detect the concentration of dissolved ozone in the liquid to verify that the liquid is adequately treated. Sensor 25 is preferably in communication with control system 30, which operates pumping system 20 and ozone generator 15. Control system 30 preferably includes a timer for timing each operation of system 10. An ozone sensor can also be arranged in this and other embodiments of my purifiers to ensure that purified liquid output does not contain more than a minimum of dissolved ozone. A timer can also be involved with control system 30 to ensure adequate deozonization of purified liquid output. Ozone sensors and timers for this purpose are preferably arranged in communication with the purified liquid storage or purified liquid output flow.

The flow of purified liquid into chamber 12 can also pass through filter 26, which can contain activated carbon or a catalyst that greatly reduces the concentration of dissolved ozone remaining in the purified liquid. This can be advantageous in situations requiring that little or no dissolved ozone remain in the liquid that is output from chamber 12. Other ways of ensuring this are to let the purified liquid stand for a few minutes in chamber 12 before using it, to aerate the purified liquid before using it, or to subject the purified liquid to ultraviolet light. By whatever method is used, the dissolved ozone concentration can be reduced before the purified liquid is output for use or consumption. For most purposes, dissolved ozone is acceptable in the treated liquid; and for some purposes, it is even desirable. No health hazard has yet been identified with directly consuming water containing dissolved ozone at levels found in system 10.

Control system 30 also preferably includes a switch that initiates operation of system 10. This can run pumping system 20 and ozone generator 15 for long enough to empty reservoir 11 and transfer purified liquid to chamber 12. Sensor 25 can verify from the presence of dissolved ozone in the passing liquid that ozone generator 15 is operating and delivering ozone to the moving liquid. If sensor 25 does not detect ozone in the liquid, a warning or indicator light could be illuminated to inform the operator, or control system 30 could shut down pumping system 20 and generator 15.

Several alternative pumping systems 20, suitable for use in system 10 of FIG. 1, are shown in FIGS. 2-4. These pumping systems can also be used in other preferred embodiments of my liquid purifier. The flow rates of liquid and gas through any pumping system used with my liquid purifier are preferably adjusted by sizing the liquid and gas conduits relative to the pumping rate and the force causing flow to occur. This eliminates the expense of detecting and metering flow rates to ensure adequate contact of liquid with ozone. The time that liquid and ozone are in contact with each other is also a factor in the purification process, since purification is a function of both the extent and the duration of ozone contact with liquid. Thus, pumping systems and liquid and gas flow lines should be selected to ensure proper flow rates of liquid and gas and adequate contact times between liquid and the ozone contained in the gas.

The pump 27 of FIG. 2 is preferably a positive displacement pump that receives the combined flows of liquid in line 16 and an ozone containing gas in line 17. Pump 27 then mixes and contacts the gas and liquid so that within pump 27 and downstream of pump 27, the liquid is in purifying contact with ozone. I have found that positive displacement pumps are good at mixing liquid and gas for contact purposes, but other types of pumps can also be used. Moreover, it is possible to use a static mixer 28 downstream of pump 27, to increase the mixing action.

Pump 31 of the embodiment of FIG. 3 is also a liquid pump and can move liquid by positive displacement or by some other pumping means. Downstream of pump 31 is a venturi 32 that draws in an ozone containing gas from line 17 to mix with and contact the liquid flowing from pump 31.

Pump 33, of the embodiment of FIG. 4, is a gas pump that forces the ozone containing gas through line 17 into chamber 34 from which a bubble line 35 extends. Gas bubbles rising in chamber 34 not only contact liquid present there, but also pump the liquid through bubble line 35 as the bubbles rise. This moves the gas and liquid mixture downstream toward gas and liquid separator 21 (not shown in FIG. 4).

Gas pump 33 is preferably arranged upstream of generator 15 so that it can force gas through generator 15, which outputs a mixture of gas and ozone. Pump 33 can also be arranged downstream of ozone generator 15, except that an ozone environment is too corrosive and problematic for most pumps to handle. Although pumping system 20 is shown in FIGS. 1 and 5-9 as downstream of generator 15, when a pumping arrangement such as shown in FIG. 4 is used for a pumping system 20, gas pump 33 is preferably arranged upstream of generator 15.

System 35, as shown in FIG. 5, uses a circulation loop to draw liquid from reservoir 36 and return liquid back to reservoir 36 while purification occurs during a circulational flow. Reservoir 36 then serves also as the purified liquid container and as the gas and liquid separator. Any ozone flowing out of reservoir 36 via vent 22 passes through ozone reducer 23, which is preferably protected by a porous hydrophobic element 24, as explained above. Reservoir 36 can be filled via a trap 37 and can have a drain 38. Sensor 25 can be located in reservoir 36 to detect the presence of dissolved ozone and communicate this to control system 30. A switch 58 can initiate a purifying operation of system 35, and control system 30 preferably includes a timer arranged for operating system 35 for a minimum duration. Output of purified liquid is preferably initiated in response to switch 39.

A filter 40 can be arranged in line 16 for liquid outflowing from reservoir 36; and in such a position, filter 40 accomplishes some liquid filtration both before and after contact with ozone, because of the circulational flow. Flowing the contents of reservoir 36 three or four times through the circulational loop that includes pumping system 20 and filter 40 is generally enough to complete the purification of the liquid. Passage through filter 40 before liquid is contacted with ozone can remove some impurities and reduce the purification load required of the ozone treatment. Passage of liquid through filter 40 after contact with ozone can remove materials precipitated by the ozone contact.

After a purifying circulation, liquid can be output from reservoir 36 by changing the route through pumping system 20 so that instead of flowing back into reservoir 36 via line 41, liquid flows to an outlet from pumping system 20. This can lead through filter 42, which can remove precipitated materials and which can reduce the concentration of any ozone still dissolved in the liquid, before the purified liquid is output from the purifier.

There are several ways that pumping system 20 can be arranged to accomplish both the purified liquid outflow and a circulational flow during purification, and one of these is shown in FIG. 6. Liquid pump 43 can pump a liquid flow to valve 44 under control of control system 30 so that during circulational flow, valve 44 directs liquid flow through venturi 45, which draws in an ozone and gas mixture and contacts it with flowing liquid on the way back to reservoir 36 through line 41. When treatment is completed and outflow is desired, valve 44 changes state, preferably in response to an outflow switch so that liquid flows directly to an outlet from pump 43. Generator 15 is preferably turned off while this occurs.

Figure 7:
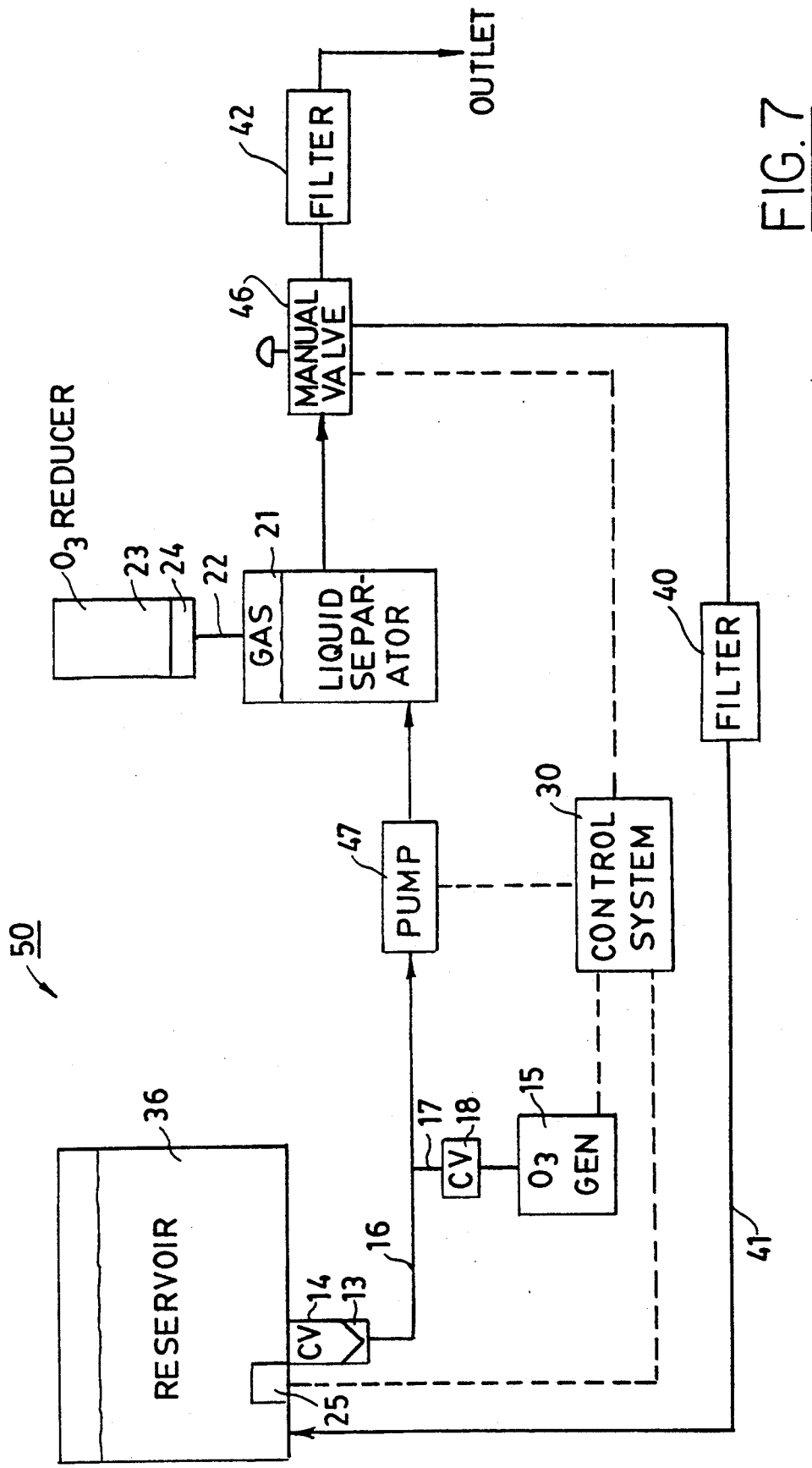
FIG. 7 shows another bypass and alternative output system, similar to the system of FIG. 5, but differing in the pumping and valving arrangement.

System 50, as shown in FIG. 7, is similar to system 35 in circulating liquid flow from and to reservoir 36. It differs in using a gas and liquid separator 21 with an ozone reducer 23 and vent 22, as explained above, and using a manually operated valve 46. This directs flow back to reservoir 36 through line 41 during purification and directs purified liquid to an outlet via filter 42. Filter 40 can be arranged in line 41 to help remove impurities during the purification flow; or, alternatively, filter 40 can be arranged in line 16 upstream of line 17 from ozone generator 15. Pump 47 is preferably a positive displacement liquid pump that pumps a gas and liquid mixture to separator 21. Control system 30 preferably includes a switch and timer and can communicate with sensor 25 in reservoir 36, as previously explained. Valve 46 is preferably arranged in communication with control system 30 so that when valve 46 is manually operated to deliver an outflow, only pump 47 is turned on, without energizing ozone generator 15. Liquid can also be output from system 50 by using a momentary electric switch that simultaneously operates pump 47 and electrically positions valve 46 to deliver an outflow.

Figure 8:
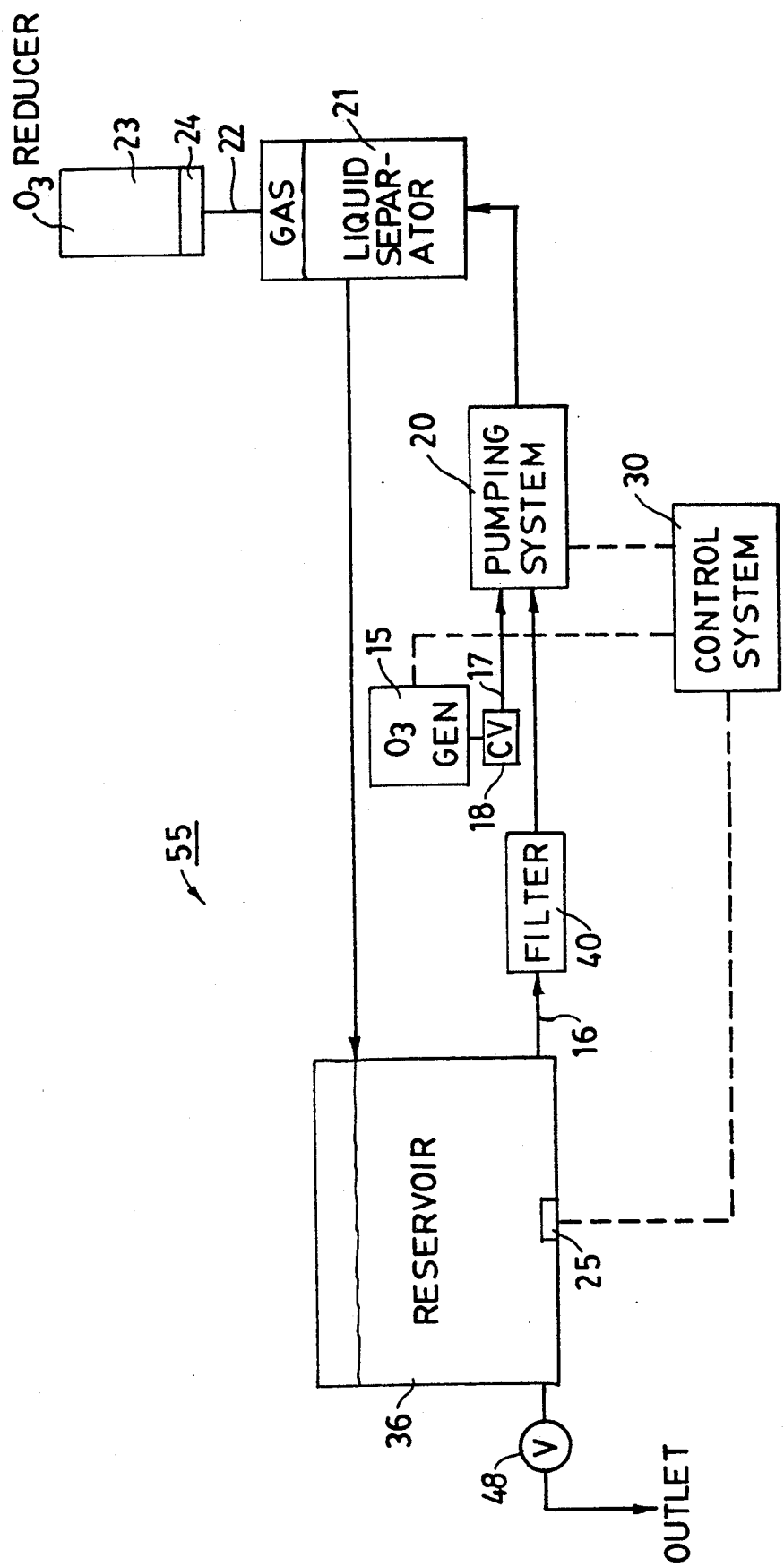
FIG. 8 shows another bypass system having a purified liquid output from the liquid reservoir.

System 55 of FIG. 8 also operates a circulational flow from and to reservoir 36 via gas and liquid separator 21, but uses pumping system 20 only to power the circulational flow during purification, and not to power the output flow. The outflow of purified liquid from reservoir 36 is via valve 48, which can be manually operated, and which uses a gravity powered outflow. Filter 40 can be arranged in the circulational loop to remove impurities from the liquid, and pumping system 20 can have any of the forms described above in FIGS. 2-4. Operation is controlled by system 30, which can communicate with sensor 25 in reservoir 36 to ensure that liquid is adequately purified.

Figure 9:
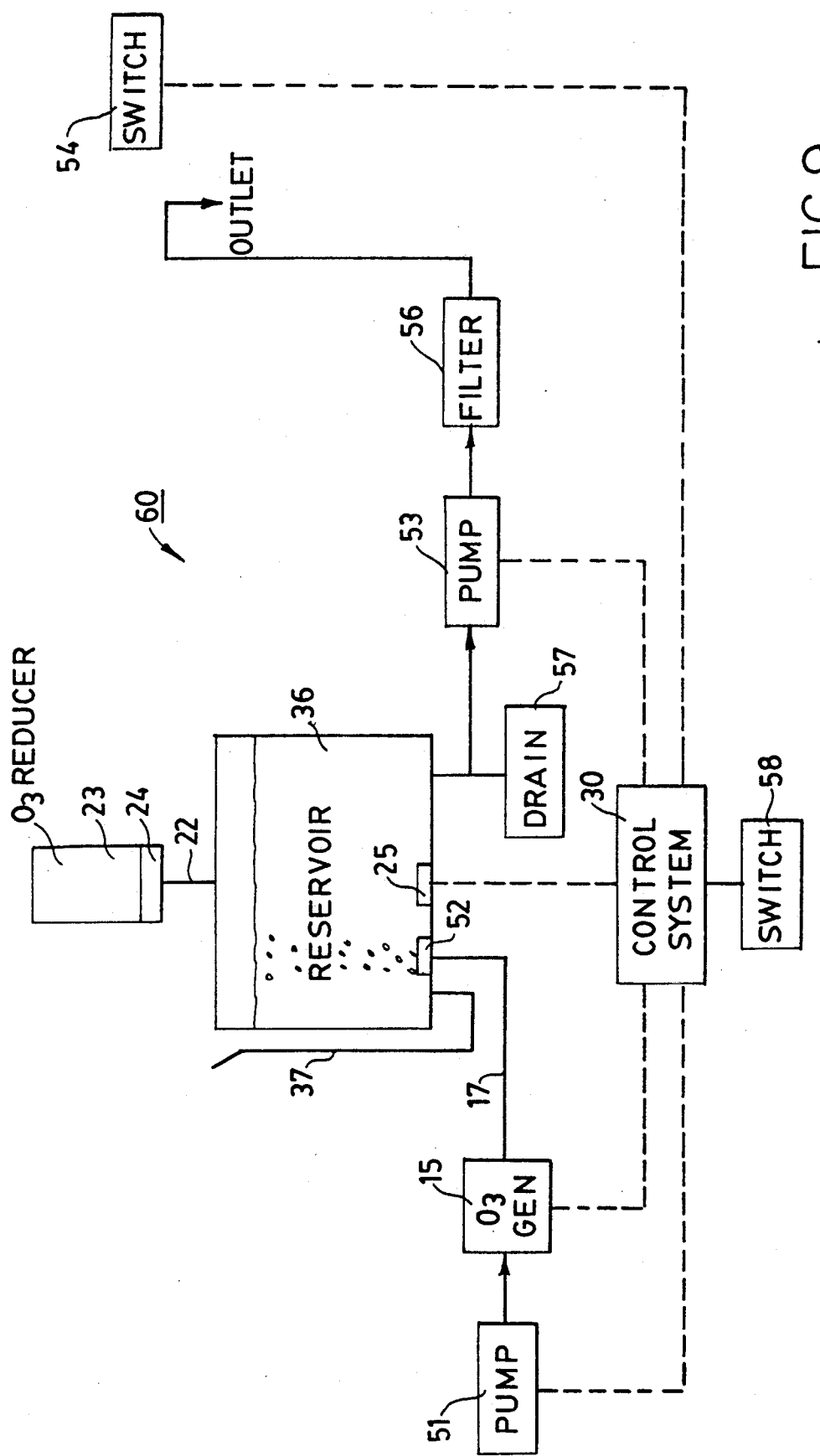
FIG. 9 shows a system using two pumps, one for pumping ozone into a reservoir for purifying liquid and another for pumping purified liquid to an outlet.

Two pumps are used in system 60 of FIG. 9. A gas pump 51 pumps an oxygen-containing gas such as ambient air, dried air, or oxygen into ozone generator 15 so that an output gas containing ozone is bubbled through diffuser 52 into the liquid in reservoir 36. The bubbles contact the liquid with ozone and accomplish its purification within reservoir 36. Diffuser 52 is porous and allows gas to flow through, preferably in a way that divides the gas flow into a multitude of bubbles. Although air stones and other materials are available for diffuser 52, I prefer a porous element made from or including a hydrophobic material that allows the ozone containing gas to flow through, but resists any flow of liquid in the opposite direction. Since a multitude of small bubbles are desirable for liquid-gas contact, and since a bubble diffuser of a given pore size produces smaller bubbles if the surface tension of the diffuser material is increased, there may be advantages in using separate materials to provide the porous hydrophobic liquid barrier and a porous bubble diffuser. For example, a hydrophilic porous material or coating on top of a porous hydrophobic material can exploit the advantages of both materials. There are also many different ways of combining porous hydrophobic liquid barriers and other porous materials producing fine diffused bubbles.

By including a porous hydrophobic material, diffuser 52 can then serve as a liquid barrier, ensuring that no liquid travels back to generator 15. This is important because the preferred form of generator 15 is a corona discharge device that would be damaged if liquid were to enter it. Trap 37, also suggested for the embodiment of FIG. 5, is preferred for adding liquid to reservoir 36.

Another way to ensure that liquid does not enter generator 15 is by directing the output from generator 15 to a level higher than the liquid level within the system so that gravity prevents liquid from flowing through the elevated passageway to generator 15. This would require that the system not be turned over while it contains liquid. A check valve can also be arranged in output line 17 from generator 15, as shown in some of the other embodiments, to help protect generator 15 from liquid.

Reservoir 36 also serves as a gas and liquid separator, allowing gas to flow through vent 22 and ozone reducer 23, which is preferably protected from liquid by porous hydrophobic element 24. Sensor 25 can detect the presence of dissolved ozone in the liquid in reservoir 36 so that control system 30 can operate the purification cycle long enough to ensure that the liquid is adequately treated.

Liquid pump 53 outputs purified liquid from reservoir 36, preferably in response to a demand switch 54 arranged near the outlet and communicating with control system 30. The purified liquid outflow through pump 53 can also pass through filter 56 to remove any precipitated impurities and to reduce the concentration of any ozone still dissolved in the purified liquid, before the liquid is output.

System 60 can be operated, by actuation of switch 58, to purify a liquid batch in reservoir 36 and then in response to switch 54 to flow the purified liquid to the outlet on demand. Reservoir 36 can be refilled on a batch basis preferably via trap 37 or from a pressurized supply line via a valve that is not shown in FIG. 9. It can also have a drain 57 and can be arranged under a countertop or in a basement below a kitchen, for example, since pump 53 allows it to deliver the outflow to a higher elevation.

I claim:

1. A batch operation purifier for contacting a liquid with an ozone containing gas, said purifier comprising:
   a. a generator that makes said ozone containing gas;
   b. a reservoir sized for holding less than 20 liters of said liquid;
   c. a liquid passageway arranged for conducting said liquid from said reservoir to a treated liquid container also sized for holding less than 20 liters;
   d. a gas passageway leading from said generator to said liquid passageway;
   e. a pumping system arranged for causing said liquid to flow through said liquid passageway and for contacting said liquid with said ozone containing gas to treat said liquid with ozone; and
   f. said pumping system and said liquid and gas passageways being sized to determine the flow rates of said liquid and said ozone containing gas.

2. The purifier of claim 1 wherein said gas passageway is connected to said liquid passageway upstream of an inlet to a pump so that said pump contacts said ozone containing gas with said liquid by mixing and pumps the mixture of said liquid and said ozone containing gas through said liquid passageway.

3. The purifier of claim 1 wherein said pump system includes a positive displacement pump for contacting said ozone containing gas with said liquid by mixing and for moving a mixture of said liquid and said ozone containing gas through said liquid passageway.

4. The purifier of claim 1 wherein said pump system includes a venturi in said liquid passageway arranged downstream from a pump, said gas passageway being connected to said venturi so that said ozone containing gas is drawn into said venturi and mixed with said liquid being moved through said venturi by said pump.

5. The purifier of claim 1 wherein said pump system includes a gas pump for pumping said ozone containing gas into said liquid passageway, and said liquid passageway includes a bubble line for moving said liquid along with bubbles of said ozone containing gas.

6. The purifier of claim 1 including a separation chamber arranged in said liquid passageway for separating said liquid from said ozone containing gas after they have been contacted.

7. The purifier of claim 1 including means for reducing the concentration of any ozone escaping into the atmosphere.

8. The purifier of claim 7 wherein a porous element including a hydrophobic material is arranged for preventing said concentration reducing means from being wetted by liquid.

9. The purifier of claim 1 including a filter arranged in said liquid passageway between said reservoir and said purified liquid container.

10. The purifier of claim 1 including means for preventing flow of liquid into said generator.

11. The purifier of claim 10 wherein said flow preventing means comprises a porous element including a hydrophobic material used as a check valve.

12. The purifier of claim 1 wherein said liquid passageway includes a contact chamber wherein said ozone containing gas is bubbled through said liquid.

13. The purifier of claim 12 wherein a porous element including a hydrophobic material is used as both a bubble diffuser for admitting said ozone containing gas into said contact chamber and also as a check valve for preventing liquid from entering said generator.

14. The purifier of claim 1 including a sensor arranged for sensing the concentration of ozone in said liquid.

15. The purifier of claim 14 including a control system responsive to said sensor for controlling the operation of said purifier.

16. The purifier of claim 1 with a control system including a timer arranged for determining a duration for each operation of said purifier.

17. The purifier of claim 1 wherein said liquid passageway includes a static mixer arranged for increasing contact between said liquid and said ozone containing gas.

18. The purifier of claim 1 including means for reducing the concentration of ozone dissolved in a purified liquid output from said purified liquid container.

19. The purifier of claim 1 including a device making said reservoir connectable to and disconnectable from said liquid passageway without loss of liquid.

20. The purifier of claim 1 including means for reducing the concentration of ozone dissolved in liquid before pumping said liquid out from said container.

21. A batch operation purifier for contacting a liquid with an ozone containing gas, said purifier comprising:
   a. a generator that makes said ozone containing gas;
   b. a reservoir sized for holding less than 20 liters of liquid;

c. a liquid passageway arranged for conducting said liquid from said reservoir to a junction;
d. a gas passageway arranged for conducting said ozone containing gas from said generator to said junction, where said ozone containing gas contacts said liquid;
e. a contact passageway arranged downstream of said junction where said liquid and said ozone containing gas can flow in contact with each other, said contact passageway being arranged for conducting said liquid back to said reservoir;
a pumping system arranged for flowing said liquid through said liquid passageway to said junction, flowing said ozone containing gas through said gas passageway to said junction, and flowing a mixture of said liquid and said ozone containing gas from said junction into said contact passageway to said reservoir so that circulation of said liquid contacts said liquid with said ozone while said liquid is enroute to said reservoir; and
g. said pumping system and said liquid and gas passageways being sized to determine the flow rates of said liquid and said ozone containing gas through said passageways.

22. The purifier of claim 21 including a sensor arranged for sensing the concentration of ozone in said liquid.

23. The purifier of claim 22 including a control system responsive to said sensor for controlling the operation of said purifier.

24. The purifier of claim 21 with a control system including a timer for determining a duration for each operation of said purifier.

25. The purifier of claim 21 wherein said pumping system includes a pump arranged downstream from said junction so that said pump contacts said ozone containing gas with said liquid by mixing.

26. The purifier of claim 21 wherein said pumping system includes a venturi downstream from a pump in said liquid passageway, said venturi constituting said junction.

27. The purifier of claim 21 wherein said pumping system includes a gas pump arranged for pumping said ozone containing gas into said liquid at said junction and including a bubble line in said contact passageway for moving liquid along with bubbles of said ozone containing gas.

28. The purifier of claim 21 wherein said liquid passageway includes a static mixer arranged for increasing contact between said liquid and said ozone containing gas.

29. The purifier of claim 21 including a separation chamber arranged in said contact passageway for separating said ozone containing gas from said liquid after they have been contacted but before the said liquid is returned to said reservoir.

30. The purifier of claim 21 including means for reducing the concentration of any ozone escaping into the atmosphere.

31. The purifier of claim 30 wherein a porous element including a hydrophobic material is arranged for preventing said concentration reducing means from being wetted by liquid.

32. The purifier of claim 21 including means for reducing the concentration of ozone dissolved in said liquid in said reservoir before dispensing purified liquid from said reservoir.

33. The purifier of claim 21 including a liquid filter arranged in a liquid flow path outside of said reservoir where said circulation of said liquid causes multiple passes of said liquid through said junction and said filter.

34. The purifier of claim 21 including means for preventing flow of liquid into said generator.

35. The purifier of claim 34 wherein said flow preventing means comprises a porous element including a hydrophobic material used as a check valve.

36. The purifier of claim 21 including a contact chamber downstream of said junction where said ozone containing gas is bubbled through said liquid.

37. The purifier of claim 36 wherein a porous element including a hydrophobic material is used both as a bubble diffuser for said contact chamber and also as a check valve preventing said liquid from entering said generator.

38. The purifier of claim 21 including a valve arranged to permit said pumping system to be used alternately to pump said liquid out of said reservoir.

39. The purifier of claim 38 including a filter arranged in an output liquid passageway.

40. The purifier of claim 21 wherein escape to the atmosphere of ozone from said reservoir is reduced by enclosing said reservoir and filling said reservoir through a liquid-filled gas trap.

41. The purifier of claim 21 including a device making said reservoir connectable to and disconnectable from said liquid passageway without loss of liquid.

42. The purifier of claim 21 including means for reducing the concentration of ozone dissolved in liquid before pumping said liquid out from said purifier.

43. A batch operation purifier for contacting a liquid with an ozone containing gas, said purifier comprising:
a. a generator that makes an ozone containing gas;
b. a chamber sized for holding less than 20 liters of said liquid; and
c. a pumping system arranged for operating during purification to pump said ozone containing gas from said generator into contact with said liquid, and for operating during output to pump said liquid out from said chamber.

44. The purifier of claim 43 including a filter arranged downstream of said chamber when said pumping system is operating during said output.

45. The purifier of claim 43 wherein said pumping system includes a gas pump operable during said purification for pumping said ozone containing gas and a liquid pump operable during said output for pumping said liquid.

46. The purifier of claim 45 including a control system arranged for operating said gas pump during said purification and an output switch arranged for operating said liquid pump during said output.

47. The purifier of claim 43 including means for reducing the concentration of any ozone escaping into the atmosphere.

48. The purifier of claim 43 including a vent from said chamber, means for reducing the concentration of any ozone escaping from said vent, and a porous element including a hydrophobic material arranged for preventing liquid from entering said vent.

49. The purifier of claim 43 including a sensor arranged for sensing the concentration of ozone in said liquid.

50. The purifier of claim 49 including a control system responsive to said sensor for controlling the operation of said purifier.

51. The purifier of claim 43 including means for preventing flow of liquid into said generator.

52. The purifier of claim 51 wherein said flow preventing means comprises a porous element including a hydrophobic material used as a check valve.

53. The purifier of claim 43 including means for reducing the concentration of ozone dissolved in liquid before pumping said liquid out from said chamber.

54. The purifier of claim 43 including means for disconnecting said chamber from said generator.

55. The purifier of claim 43 with a control system including a timer arranged for determining a duration for each operation of said purifier.

* * * * *